US011422128B2

(12) United States Patent
Shimizu et al.

(10) Patent No.: US 11,422,128 B2
(45) Date of Patent: Aug. 23, 2022

(54) IMMUNOASSAY EMPLOYING SULFATED POLYSACCHARIDE

(71) Applicant: LSI Medience Corporation, Chiyoda-ku (JP)

(72) Inventors: Ryuhei Shimizu, Chiyoda-ku (JP); Keiichi Shoji, Chiyoda-ku (JP); Xu Zhang, Chiyoda-ku (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 199 days.

(21) Appl. No.: 16/092,684

(22) PCT Filed: Apr. 12, 2017

(86) PCT No.: PCT/JP2017/014943
§ 371 (c)(1),
(2) Date: Oct. 10, 2018

(87) PCT Pub. No.: WO2017/179611
PCT Pub. Date: Oct. 19, 2017

(65) Prior Publication Data
US 2019/0145965 A1 May 16, 2019

(30) Foreign Application Priority Data
Apr. 13, 2016 (JP) .............................. JP2016-080660

(51) Int. Cl.
*G01N 33/53* (2006.01)
*G01N 33/48* (2006.01)
*G01N 33/531* (2006.01)

(52) U.S. Cl.
CPC ......... *G01N 33/5306* (2013.01); *G01N 33/48* (2013.01); *G01N 33/53* (2013.01); *G01N 33/531* (2013.01)

(58) Field of Classification Search
CPC .. G01N 33/531; G01N 33/5306; G01N 33/48; G01N 33/53; G01N 33/54333; G01N 2400/22; G01N 2400/40; G01N 2400/18
See application file for complete search history.

(56) References Cited

U.S. PATENT DOCUMENTS

| 4,829,009 | A |   | 5/1989 | Graves |           |
|-----------|---|---|--------|--------|-----------|
| 5,466,580 | A | * | 11/1995 | White | G01N 33/56911 |
|           |   |   |         |       | 435/7.1   |
| 8,617,820 | B2 | * | 12/2013 | Sankaran | G01N 33/54393 |
|           |   |   |         |       | 435/7.1   |
| 2005/0221404 | A1 |   | 10/2005 | Lane |  |
| 2010/0258440 | A1 |   | 10/2010 | Sugiyama |  |
| 2011/0104825 | A1 | * | 5/2011 | Yamamoto | G01N 33/5306 |
|           |   |   |         |       | 436/533  |
| 2012/0045847 | A1 |   | 2/2012 | Lewisch et al. |  |
| 2013/0035288 | A1 |   | 2/2013 | Turecek |  |
| 2013/0330841 | A1 |   | 12/2013 | Okamura |  |
| 2015/0369799 | A1 |   | 12/2015 | Miyazawa |  |
| 2016/0018390 | A1 | * | 1/2016 | Zielinski | G01N 33/82 |
|           |   |   |         |       | 435/7.91 |
| 2018/0284133 | A1 |   | 10/2018 | Tokunaga et al. |  |

FOREIGN PATENT DOCUMENTS

| CN | 1643381 | A |   | 7/2005 |  |
|----|---------|---|---|--------|--|
| CN | 102047104 | A |   | 5/2011 |  |
| CN | 103841979 | A |   | 6/2014 |  |
| EP | 2952896 | A1 | * | 12/2015 | ......... G01N 33/5306 |
| JP | S6270761 | A |   | 4/1987 |  |
| JP | S6367864 | B2 |   | 12/1988 |  |
| JP | H08226920 | A |   | 9/1996 |  |
| JP | 2001524084 | A |   | 11/2001 |  |
| JP | 2002502979 | A |   | 1/2002 |  |
| JP | 2006524319 | A |   | 10/2006 |  |
| JP | 2007170992 | A |   | 7/2007 |  |
| JP | 2010107363 | A |   | 5/2010 |  |
| JP | 2010127827 | A |   | 6/2010 |  |
| JP | 2011007782 | A |   | 1/2011 |  |
| JP | 5189067 | A |   | 4/2013 |  |
| JP | 2013152247 | A |   | 8/2013 |  |
| WO | WO-9221769 | A1 | * | 12/1992 | ....... G01N 33/54393 |
| WO | 2002063302 | A1 |   | 8/2002 |  |
| WO | 2005121795 | A1 |   | 12/2005 |  |

OTHER PUBLICATIONS

International Search Report issued in PCT/JP2017/014943, dated Jul. 4, 2017.
Detamina CL IL-2R, Kyowa Medex Co., Ltd., 2011.
Siemens Immulyze IL-2R II, Siemens Healthcare Diagnostics Kabushiki Kaisha, 2015.
De Jongh R, "The Effects of Anticoagulation and Processing on Assays of IL-6, sIL-6R, sIL-2R and Soluble Transferrin Receptor," Cytokine, 1997, vol. 9 No. 9, pp. 696-701.
Collinson, P O, "Rapid troponin T measurement in whole blood for detection of myocardial damage," Ann Clin Biochem, 1995, vol. 32, No. 5, pp. 454-458.
Serufuri N IL-2R, Kyowa Medex Co., Ltd., 2010.
Takano, Ryo, "Sulfation and Desulfation of Polysaccharides: Effects of the Modification on their Properties," Kagaku to Seibutsu, 1996, vol. 34, No. 9, pp. 598-604.

(Continued)

*Primary Examiner* — Shafiqul Haq
(74) *Attorney, Agent, or Firm* — Heslin Rothenberg Farley & Mesiti P.C.

(57) ABSTRACT

Regardless of the type of specimen, such as a serum or heparinized plasma containing different anticoagulants, which are widely used in general, when a substance to be measured (for example, sIL-2R) in a biological sample is immunologically detected, a measuring method and a kit capable of stably obtaining with high accuracy, unaffected by interfering substances in the specimen, are provided. An immunocomplex between the substance to be measured and an antibody that specifically binds to the substance to be measured is formed in the presence of a sulfated polysaccharide. The kit comprises an antibody that specifically binds to the substance to be measured, and a buffer containing a sulfated polysaccharide.

5 Claims, No Drawings

(56) References Cited

OTHER PUBLICATIONS

Extended European Search Report mailed in connection with European Patent Application No. 17782424.0 dated Nov. 11, 2019.
Cyclodextrin, Wikipedia entry, downloaded from internet URL https://en.wikipedia.org/wiki/Cyclodextrin on Sep. 7, 2021.
3-Cyclodextrin sulfate, Sigma-Aldrich catalog entry, downloaded from internet at URL https://www.sigmaaldrich.com/US/en/product/SIGMA/T3821 on Sep. 7, 2021.
Dextran, Wikipedia entry, downloaded from internet URL https://en.wikipedia.org/wiki/Dextran on Sep. 7, 2021.
Dextran sulfate, Biosynth Carbosynth catalog entry, downloaded from internet URL https://www.carbosynth.com/carbosynth/website.nsf/(w-productdisplay)/2AF4293515B308A080257ADB004C2528 on Sep. 7, 2021.

* cited by examiner

IMMUNOASSAY EMPLOYING SULFATED POLYSACCHARIDE

CROSS REFERENCE TO RELATED APPLICATIONS

This application is a U.S. National Phase filing under 35 U.S.C. § 371 of International Application PCT/JP2017/014943, filed Apr. 12, 2017, and published as WO2017/179611 A1 on Oct. 19, 2017. PCT/JP2017/014943 claims priority from Japanese Patent Application Number 2016-080660, filed Apr. 13, 2016. The entire contents of each of these applications are hereby incorporated herein by reference.

TECHNICAL FIELD

The present invention relates an immunological measuring method and a kit capable of inhibiting a difference in measurement values between different test samples, using a sulfated polysaccharide.

BACKGROUND ART

In an immunological measuring method in which an analyte is optically measured by an antigen-antibody reaction, a phenomenon in which measured values are different, for example, between a serum test sample and a plasma test sample, due to the difference of blood collection tubes used, is confirmed, and it sometimes becomes a problem. The cause of difference varies depending on the items to be measured, and as one of the known findings, the influence of insolubilization of fibrinogen contained in plasma on the measurement value of a plasma test sample can be mentioned. It is known that the influence is avoided by adding a chelating agent with a coordination number of 3 or less to a reaction system containing a surfactant (Patent literature 1).

Further, a blood sample (a serum, plasma, or whole blood) is generally used for evaluating, for example, various cardiac troponins. However, this selection is limited depending on a method used, for example, because it is known that a serum is an inappropriate biological sample for the method of quickly evaluating cardiac troponin, and that whole blood makes a quantitative assay difficult to perform. In an immunological measurement using heparinized plasma or heparinized whole blood, even when the performance of the method used is very high, unreliable results are often obtained. In general, if the cardiac troponin concentration in plasma is not very high, such a problem occurs (Non-patent literature 1). Indeed, it is known that the presence of heparin in a blood sample interferes during various immunological measurements, and affects the measurement results, and as a result, the physician's clinical diagnosis may be modified.

Until now, with respect to a method of avoiding the influence of interfering substances contained in a specimen in a cardiac troponin assay, an immunological measuring method characterized in that it is carried out against a heparin-containing biological sample in the presence of hexadimethrine bromide (polybrene) is disclosed (Patent literature 2). However, it was insufficient to stably measure clinical specimens.

CITATION LIST

Patent Literature

Patent literature 1—Japanese Patent No. 5189067
Patent literature 2—Japanese Unexamined Patent Publication (Kokai) No. 2010-107363

Non-Patent Literatures

Non-patent literature 1—P.O. Collison et al., Ann. Cli. Biochem., (1995), 32, pp. 454-458

SUMMARY OF INVENTION

Technical Problem

As described in detail in the Examples below, the present inventors attempted to measure a soluble interleukin-2 receptor (hereinafter sometimes abbreviated as sIL-2R) in biological samples (a serum and heparinized plasma), and noticed a difference in the measured values, caused by the different types of test samples for measurement (hereinafter sometimes referred to as specimens) prepared from the biological samples.

The object of the present invention is, regardless of the type of test samples, such as a serum or heparinized plasma containing different anticoagulants, which are generally widely used, when a substance to be measured (for example, sIL-2R) in a biological sample is immunologically detected, to provide a measuring method and a kit capable of stably obtaining with high accuracy, unaffected by interfering substances in the test sample.

Solution to Problem

Under these circumstances, the present inventors conducted intensive studies, and found that, in a method of immunologically measuring sIL-2R in a serum and heparinized plasma, regardless of the type of test samples, it was possible to stably obtain measurement values with high accuracy, unaffected by interfering substances in the test samples, by measuring sIL-2R under conditions where a sulfated polysaccharide was added to a reaction solution, and the present invention was completed. In particular, it was unexpected results that such effects could not be obtained in the coexistence of a polysaccharide without a sulfate group and a compound without a polysaccharide but having a sulfate group, but could be obtained in the presence of the sulfated polysaccharide. Further, although B/F separation was carried out, when the sulfated polysaccharide did not coexist, the measurement was affected by interfering substances contained in the test sample. It was considered from the results that the interfering substances were not insolubilization of fibrinogen, the influence of hemoglobin, or the like, which was previously known.

The present invention can be exemplified as follows:
1. a method of immunologically measuring a substance to be measured in a biological sample, characterized in that an immunocomplex between the substance to be measured and an antibody that specifically binds to the substance to be measured is formed in the presence of a sulfated polysaccharide,
2. a method of reducing a difference in a method of immunologically measuring a substance to be measured in a biological sample, said difference being the difference between a measurement value when using a blood sample to which heparin is added as an anticoagulant and a measurement value when using a serum, characterized in that an immunocomplex between the substance to be measured and an antibody that specifically binds to the substance to be measured is formed in the presence of a sulfated polysaccharide, 3. the method of [1] or [2], wherein the sulfated polysaccharide is dextran sulfate or β-cyclodextrin sulfate, 4. the method of any one of [1] to [3], wherein the sulfated polysaccharide is contained in a solution for diluting specimen and/or an antibody solution, 5. the method of any one of [1] to [4], comprising the step of B/F separation of the formed immunocomplex, 6. the method of any one of [1] to [5], comprising bringing the substance to be measured into contact with a first antibody and a second antibody that specifically bind to the substance to be measured, and measuring the immunocomplex formed by an antigen-antibody reaction, 7. the method of any one of [1] to [6], wherein the substance to be measured is soluble interleukin-2 receptor or prostate specific antigen, 8. a kit for measuring a substance to be measured, for the method of any one of 1 to 7, said kit comprising an antibody that specifically binds to the substance to be measured, and a buffer containing a sulfated polysaccharide, 9. the kit of 8, comprising an antibody carried on a magnet particle, as the antibody that specifically binds to the substance to be measured, and 10. the kit of [8] or [9], wherein the substance to be measured is soluble interleukin-2 receptor or prostate specific antigen.

Advantageous Effects of Invention

Regardless of the type of test samples (a serum and heparinized plasma), which are generally widely used, a substance to be measured (for example, sIL-2R) in a biological sample can be stably measured with high accuracy by using the method and the reagent kit of the present invention, unaffected by interfering substances in the test sample.

DESCRIPTION OF EMBODIMENTS

The biological sample in the present invention is a sample collected from a human being or the like, and is suspected of containing a substance to be measured (for example, sIL-2R). As the biological sample, blood samples, such as whole blood, a serum, plasma, and the like, may be exemplified, and in particular, it is preferable that a serum and heparinized plasma are included in the test samples.

The test sample (specimen), which can be used in the present invention, is not particularly limited, so long as it is a sample for measurement that can be prepared from the above-mentioned biological sample. When a blood sample is targeted, specimens obtained using an anticoagulant, such as whole blood, a serum, plasma, and the like, may be exemplified. As the anticoagulant, heparin, EDTA, citric acid, and the like, may be exemplified. Preferably, the anticoagulant can be used by adding it to a blood collection tube or the like in advance, when collecting blood from a subject to be measured, such as a human. In particular, when a serum and heparinized plasma are targeted in parallel, it is preferable because the effect of the present invention is high.

The substance to be measured, which is targeted in the present invention, is not particularly limited, so long as it is a substance capable of being measured by an immunological measuring method. For example, a protein, a glycoprotein, a lipid protein, a receptor, an enzyme, a viral antigen, an antiviral antibody, and the like, may be exemplified, and more particularly, soluble interleukin-2 receptor (sIL-2R), prostate specific antigen (PSA), hepatitis B virus surface antigen (HBsAg), hepatitis C virus (HCV) antibody and antigen, human immunodeficiency virus (HIV) antibody, human T cell leukemia virus-1 (HTLV-1) antibody, Treponema pallidum (TP) antibody, and the like; various myocardial markers (creatine kinase (CKMB), myoglobin, troponin); various hormones, and the like. The soluble interleukin-2 receptor is preferable. The soluble interleukin-2 receptor is a receptor involved in the immune response, for example, it is mainly present on the membrane of T cells, which are immune cells, and promotes the activation of T cell function by forming a complex with interleukin-2 as its ligand. The interleukin-2 receptor has three subtypes, and it is known that an α subunit therein is isolated from the cell membrane, and is present in blood. Since the soluble interleukin-2 receptor maintains a binding property with interleukin-2, it is considered that it is also involved in immune regulation of a living body, and it is mainly used as a marker for acute leukemia in clinical practice.

The immunological measuring method, which can be used in the present invention, is not particularly limited, so long as it is a known method using an antibody specific to a substance to be measured. For example, a turbidimetric immunoassay (TIA), an enzyme immunoassay (EIA), a radioimmunoassay (RIA), a latex agglutination method, a fluorescent immunoassay, an immunochromatography, and the like, may be exemplified. More particularly, it is a method in which an immunocomplex of a substance to be measured contained in a test sample with an antibody specific to the substance to be measured is formed in a reaction solution, and the presence of the substance to be measured is detected by appropriately detecting a signal caused by the formation. Although the antibody may be determined depending on the measurement system, a sandwich immunological measuring method (a sandwich immunoassay) using two or more antibodies may be selected for a quantitative measurement with high sensitivity. The sandwich immunological measuring method may be carried out in one or more stages (two stage, three stage, or the like). For example, a method comprising the step of forming an immunocomplex of a substance to be measured with an antibody that specifically binds to the substance to be measured and that is carried on an insoluble carrier for B/F separation, the step of B/F separation of the immunocomplex, and the step of measuring the separated immunocomplex, may be exemplified.

For example, when sIL-2R contained in a biological sample is targeted as the substance to be measured, the measurement of sIL-2R may be carried out by preparing a specimen from the biological sample, as described above; preparing a specimen for measurement from the specimen using a specimen dilution solution; forming an immunocomplex by mixing an insoluble carrier on which an antibody that specifically binds to sIL-2R (a first antibody), and another sIL-2R-specific antibody that is different from the first antibody and labeled with a substance for labeling (a second antibody); removing an unreacted antibody and sIL-2R by washing (B/F separation); and measuring the amount of the labeled substance bound to the insoluble carrier.

As the insoluble carrier, a carrier generally used in the art may be used. As a material of the insoluble carrier, for example, polymer materials, such as latex, rubber, polyethylene, polypropylene, polystyrene, styrene-butadiene copolymer, polyvinyl chloride, polyvinyl acetate, polyacrylamide, polymethacrylate, styrene-methacrylate copolymer, polyglycidyl methacrylate, acrolein-ethylene glycol dimethacrylate copolymer, polyvinylidene difluoride (PVDF), silicone, or the like; agarose; gelatin; erythrocyte; inorganic materials, such as silica gel, glass, inert alumina, magnetic material, or the like; or the like, may be exemplified. These materials may be used alone, or as a combination of two or more.

As the form of the insoluble carrier, a microtiter plate, a test tube, beads, particles, nanoparticles, or the like, may be exemplified. As the particles, magnetic particles, hydrophobic particles such as polystyrene latex, copolymer latex particles having hydrophilic groups, such as an amino group, a carboxyl group, and the like, on the surface, erythrocytes, gelatin particles, or the like, may be exemplified. Among them, magnetic particles are particularly preferred from the viewpoint of rapid and convenient B/F separation, and more particularly, magnetic particles of microparticles or the like, made of metals, such as ferric oxide ($Fe_3O_4$), diiron trioxide ($Fe_2O_3$), various ferrites, iron, manganese, nickel, cobalt, chromium, or the like; or alloys, such as cobalt, nickel, manganese, or the like, may be preferably used. Further, these magnetic particles in the form that they are contained inside polymer latex such as polystyrene or the like, gelatin, liposomes or the like, or in the form that they are immobilized on the surface, may be preferably used.

The method of immobilizing the first antibody on these insoluble carriers is known in the art. The immobilization may be carried out by, for example, a physical adsorption method, a covalent bonding method, an ionic bonding method, or combinations thereof.

The substance for labeling is not particularly limited, so long as it is a substance for labeling that may be used in a conventional immunological measuring method. For example, an enzyme, a fluorescent substance, a radioactive isotope, an insoluble particulate substance, or the like, may be exemplified. As the enzyme for labeling, alkaline phosphatase, peroxidase, glucose oxidase, tyrosinase, acid phosphatase, or the like, may be exemplified. As the fluorescent substance, fluorescein isothiocyanate (FITC), green fluorescent protein (GFP), luciferin, or the like, may be exemplified. As the radioactive isotope, $^{125}I$, $^{14}C$, $^{32}P$, or the like, may be exemplified.

In the case that the substance for labeling is an enzyme, the substance for labeling can be measured by carrying out a luminescence, fluorescence, or coloring reaction using a substrate for the enzyme. In the case that the enzyme is alkaline phosphatase, as the substrate, a chemiluminescent substrate, such as CDP-star (registered trademark)(disodium 4-chloro-3- (methoxyspiro{1,2-dioxetane-3,2' -(5'-chloro) tricyclo[3.3.1.1$^{3, 7}$]decan}-1-4-yl)phenyl phosphate), CSPD (registered trademark)(disodium 3-(4-methoxyspiro{1,2-dioxetane-3,2-(5'-chloro)tricyclo[3.3.1.1$^{3, 7}$]decane}-4-yl) phenylphosphate), AMPPD (registered trademark)(adamantyl methoxyphenyl phosphoryl dioxycetane), APS-5, or the like; a fluorescent substrate, such as 4-methylumbelliferylphosphate or the like; a chromogenic substrate, such as p-nitrophenyl phosphate, BCIP (5-bromo-4-chloro-3-indolyl-phosphoric acid), NBT (4-nitro blue tetrazolium chloride), INT (iodo-nitrotetrazolium), or the like, may be used.

As the antibody that specifically binds to a substance to be measured, which may be used in the present invention, those skilled in the art may appropriately select and use a known antibody. For example, an antibody that specifically binds to sIL-2R is not particularly limited, so long as it is a monoclonal antibody or polyclonal antibody that recognizes the amino acid sequence, the three-dimensional structure, or the like of sIL-2R as its epitope. For example, antibody AM92.3 (manufactured by Pierce), monoclonal antibody 7G7/B6 (manufactured by Pierce), MAB223 (manufactured by R&D Systems), MAB623 (manufactured by R&D Systems), MAB1020 (manufactured by R&D Systems), YNRhIL2R (manufactured by SANTA CRUZ BIOTECHNOLOGY), IL2R.1 (manufactured by Abcam), B-B10 (manufactured by Lifetechnologies), EPR6452 (manufactured by Genetex), OAPA00004 (manufactured by AVIVA system biology), DM254-05 (manufactured by Acris antibodies), or the like, may be exemplified.

These antibodies may be prepared in accordance with a known method. For example, in the case of sIL-2R, an animal is immunized with sIL-2R purified from human T cells, recombinant sIL-2R prepared in vitro, or the like, as an antigen, to prepare an antibody, and further, its epitope may be determined. The epitope means not only the minimum region recognized by an antibody, but also a region identified as the recognizable region by an antibody. Further, an antibody fragment such as Fab or the like, which may be prepared by a known method, may be used. These antibodies may be appropriately purchased from Genway Biotech, Diaclone, Santa Cruz, R&D Systems, or the like.

In the case that two types of antibodies are used in the measurement of the present invention, the antibodies are not limited, so long as they can form an immunocomplex with the substance to be measured (for example, sIL-2R) contained in a biological sample, but it is preferable that the epitopes recognized by the first antibody and the second antibody are different from each other. Further, a monoclonal antibody and a polyclonal antibody may be used as an appropriate combination thereof. Further, each of the first antibody and the second antibody is not limited to one kind of antibody, and two or more antibodies may be used as each thereof.

In the immunological measuring method described above, the addition of a sulfated polysaccharide in the present invention may be carried out so that the sulfated polysaccharide is present at least during the first immunocomplex formation (in the reaction solution) of the substance to be measured (for example, sIR-2R) and the antibody that specifically binds to the substance to be measured (for example, sIR-2R). More particularly, the sulfated polysaccharide may be added simultaneously at the time of the immunocomplex formation (in the reaction solution), or may be added to the specimen before the immunocomplex formation (before contact between the antibody and the specimen containing the substance to be measured).

The sulfated polysaccharide to be added may be prepared as a solution by dissolving it in a known buffer. Besides the buffer, it may be prepared alone, or it may be prepared together with a known substance(s) required in a pretreatment of the specimen, or at the reaction. Since the sulfated polysaccharide may be added at least during the immunocomplex formation (in the reaction solution), as described above, it may be contained in a buffer or the like that can be present at that time. The buffer or the like that can be present at the immunocomplex formation may be appropriately selected depending on a measuring method and an instrument used, but a specimen dilution solution, an antibody solution (a solution of antibody-immobilized particles, a labeled-antibody solution, or the like), or the like, may be exemplified. Further, the sulfated polysaccharide may be added to multiple buffers.

As the sulfated polysaccharide in the present invention, dextran sulfate, β-cyclodextrin sulfate, N-acetyl heparin (NAH), N-acetyl-de-O-sulfated-heparin (NA-de-o-SH), de-N-sulfated-heparin (De-NSH), de-N-sulfated-acetylated-heparin (De-NSAH), periodic acid-oxidized heparin (POH), chemical sulfated laminarin (CSL), chemical sulfated alginic acid (CSAA), chemical sulfated pectin (CSP), heparin-derived oligosaccharide (HDO), pentosan polysulfate (PPS), fucoidan, and the like, may be exemplified. Preferably, dextran sulfate and β-cyclodextrin sulfate may be exemplified. The sulfated polysaccharide may be added in any form, if it is provided so that it can exist as ions in the reaction solution. For example, polysaccharide of sulfated chloride or polysaccharide of sulfated bromide may be exemplified, and more particularly, the coexistence with lithium chloride, sodium chloride, potassium chloride, calcium chloride, magnesium chloride, ammonium chloride, lithium bromide, sodium bromide, potassium bromide, calcium bromide, magnesium bromide, ammonium bromide, or the like, may be exemplified, and sodium chloride is preferable.

The concentration of the sulfated polysaccharide in the present invention, as the concentration at the time of the immunocomplex formation, may be selected as an appropriately combination from the group consisting of more than 0.0000004%, 0.000004% or more, preferably 0.00004% or more, more preferably 0.0004% or more, still more preferably 0.004% or more, still more preferably 0.04% or more, still more preferably 0.01% or more, and still more preferably 0.02% or more; and 1% or less, preferably 0.4% or less, and more preferably 0.04% or less. In the present invention, regardless of the presence of sulfated polysaccharides in a biological sample (for example, heparin in heparinized plasma), the sulfated polysaccharide in the reaction solution is allowed to exist in the above concentration range. In connection with this, care must be taken, because if the sulfated polysaccharide in the reaction solution is increased too much, the antigen-antibody reaction is suppressed (inhibited) and desired measurement cannot be performed with high accuracy. In order to stably measure sIL-2R in a biological sample with high accuracy regardless of the type of specimen in accordance with the present invention, it is a range of design to determine the concentration to be added depending on the amount of the substance to be measured (for example, sIL-2R) contained in the specimen, and the sulfated polysaccharide used. For example, 0.000004% or more and 0.04% or less for dextran sulfate (molecular weight: 20,000), 0.0004% or more and 0.04% or less for dextran sulfate (molecular weight: 4,000), 0.02% or more and 0.4% or less for β-cyclodextrin sulfate, and the like, may be exemplified.

As shown in the Examples below, the concentration and the kind of the sulfated polysaccharide in the present invention may be easily determined for those skilled in the art, by preparing a blood sample to which heparin is added (heparinized plasma) and other samples (a serum); measuring the substance to be measured (for example, sIL-2R) in each blood sample in the presence of several different concentrations of sulfated polysaccharide; and determining the concentration range of the sulfated polysaccharide where measured values of both samples are consistent with each other. That is to say, the concentration and the kind of the sulfated polysaccharide in the present invention may be selected from the concentration range where a measured value obtained when using a blood sample to which heparin as an anticoagulant is added (heparinized plasma) is consistent with a measured value obtained when using other samples (a serum). The fact that measured values are consistent with each other means concretely that the measured value (an optical count provided with a measurement instrument, a concentration calculated using a standard, or the like) is within the range between −10% and +10%. In general, it can be considered clinically useful, if it is within the range.

The kit of the present invention may be used for carrying out the method of the present invention, and comprises an antibody that specifically binds to a substance to be measured (for example, sIL-2R), and a buffer containing a sulfated polysaccharide.

As the antibody that specifically binds to a substance to be measured, a known antibody described above may be used, and either a monoclonal antibody or a polyclonal antibody may be used. Further, an antibody fragment maintaining a binding property specific to cardiac troponin, for example, Fab, Fab', F(ab')$_2$, or Fv, may be used in the kit.

Further, the antibody may be used in the kit as it is, or in a form suitable for an immunological method used. For example, it may be used in the kit, in a state of being immobilized to a latex carrier, when using a latex agglutination method; in a state of being immobilized to magnetic particles, when using a high sensitivity measuring method using magnetic particles or the like; in a state of being immobilized to a substrate, when using an immunochromatography or the like using a substrate; or in a state of being labeled, when labeling with a labeling substance (an enzyme, a fluorescent substance, a chemiluminescent substance, a radioactive isotope, biotin, or avidin) is necessary.

As mentioned above, as the buffer containing the sulfated polysaccharide, for example, a specimen dilution solution, an antibody solution (a solution of antibody-immobilized particles or a labeled-antibody solution), or the like, may be exemplified. The specimen dilution solution is preferred.

The kit of the present invention can comprise an instruction manual, in which explanation on the procedures of the immunological measuring method using the kit of the present invention, precautions concerning storage, handling, and the like of the kit per se, or the like, are stated.

EXAMPLES

The present invention will now be further illustrated by, but is by no means limited to, the following Examples.

Referential Example 1: Preparation of reagent for measuring soluble interleukin-2 receptor and measurement.

Referential Example 1-1: Preparation of reagent for measuring soluble interleukin-2 receptor and samples to be measured.

A reagent for measuring a soluble interleukin-2 receptor (sIL-2R) was prepared.

Specimen dilution solution: A buffer containing 0.1 mol/L HEPES (8.0), 0.15 mol/L NaCl, and 0.05% Tween20 was used.

First antibody solution: A magnetic-particle solution containing magnetic latex particles (JSR) on which a mouse monoclonal antibody (manufactured by R&D Systems) that recognized sIL-2R was immobilized was used.

Second antibody solution: A labeled-antibody solution containing another mouse monoclonal antibody (manufactured by R&D Systems) that recognized sIL-2R and was labeled with alkaline phosphatase (ALP) by a maleimide method was used.

Luminescent substrate solution: CDP-star (manufactured by Applied Biosystems) was used.

B/F washing solution: A buffer containing 0.01 mol/L MOPS (7.5), 0.15 mol/L NaCl, and 0.05% Triton X-100 was used.

Samples to be measured (specimens): A serum and heparinized plasma obtained from a healthy person in accordance with a conventional method were used.

Referential Example 1-2: Measurement with reagent for measuring soluble interleukin-2 receptor.

Measurement using automated clinical testing system (STACIA: manufactured by LSI Medience Corporation).

STACIA special bottles were individually filled with the above-prepared specimen dilution solution, first antibody solution (magnetic latex reagent), and second antibody solution (enzyme-labelled antibody reagent), and were set in the instrument. The measurement was carried out in accordance with the operation method of the instrument as follows:

More particularly, 50 μL of the specimen dilution solution was added to 5 μL of a specimen, and heated at 37° C. for 3.5 minutes, and then, 25 μL of the first antibody solution (magnetic latex reagent) was added thereto, and heated at 37° C. for 4.2 minutes. sIL-2R in the specimen was reacted with the first antibody (magnetic latex) to form a magnetic latex-sIL-2R complex. Next, 50 μL of the second antibody solution (enzyme-labelled antibody reagent) was added thereto, and heated at 37° C. for 4.4 minutes. When the second antibody solution (ALP-labeled antibody) was added thereto, the ALP-labeled antibody was reacted with the magnetic latex-sIL-2R complex to form a magnetic latex-sIL-2R-ALP-labeled antibody complex. After unreacted antibodies and sIL-2R were removed by washing (B/F separation), 100 μL of the luminescent substrate solution was added thereto. After a reaction at 37° C. for 2.7 minutes, the amount of luminescence was measured. When CDP-Star was added, CDP-Star was hydrolyzed by ALP contained in the complex to emit light. In the detection, the luminescence count of the chemiluminescent substrate detected by a photomultiplier tube (PMT) was regarded as the measurement result.

Example 1: Effect of addition of sulfated polysaccharide, polysaccharide without sulfate group, or compound without polysaccharide but having sulfate group to reaction solution on reactivity of sIL-2R.

The measurement was carried out in accordance with Referential Example 1, except that any one of sulfated polysaccharides, polysaccharides without a sulfate group, or compounds without a polysaccharide but having a sulfate group was added to the specimen dilution solution so as to be the following concentrations in the reaction solution.

Sulfated polysaccharides: Dextran sulfate (molecular weight: 4000) was added to the specimen dilution solution so as to be 0.04%. β-Cyclodextrin sulfate was added to the specimen dilution solution so as to be 0.04%.

Polysaccharides without a sulfate group: Dextran was added to the specimen dilution solution so as to be 0.04%. Cyclodextrin was added to the specimen dilution solution so as to be 0.04%.

Compounds without a polysaccharide but having a sulfate group: CHAPSO was added to the specimen dilution solution so as to be 0.04%. Sodium octanoate was added to the specimen dilution solution so as to be 0.04%. The measurement was carried out in accordance with Referential Example 1, except for the above.

The results are shown in Table 1. The value obtained by dividing the count of the heparinized plasma by the count of the serum and then multiplying it by 100 was shown as heparinized plasma/serum. In the case of no addition, it was found that the reactivity of the soluble interleukin-2 receptor was different from each other, between the serum and the heparinized plasma. Further, in the case of polysaccharides having sulfate groups (sulfated polysaccharides), such as dextran sulfate (molecular weight: 4000), (β-cyclodextrin sulfate, or the like, the reactivity in the serum was consistent with that in the heparinized plasma (heparinized plasma/serum was 99% or 100%), but in the case of only polysaccharides without a sulfate group, such as dextran, cyclodextrin, or the like, or compounds without a polysaccharide but having a sulfate group, such as CHAPSO, sodium octanoate, or the like, the reactivity in the serum was inconsistent with that in the heparinized plasma (heparinized plasma/serum was 130% to 138%). It was shown that the addition of a polysaccharide having sulfate groups was necessary to make the reactivity in the serum consistent with that in the heparinized plasma.

TABLE 1

| | No addition | Dextran sulfate (4,000) | β-Cyclodextrin sulfate | Dextran (2,000) | Cyclodextrin | CHAPSO | Sodium octanoate |
|---|---|---|---|---|---|---|---|
| Serum sample (count) | 15544 | 21591 | 21328 | 16185 | 16156 | 15508 | 16224 |
| Heparinized plasma serum (count) | 20779 | 21462 | 21310 | 21112 | 22316 | 20981 | 21349 |
| heparinized plasma/serum | 134% | 99% | 100% | 130% | 138% | 135% | 132% |

Example 2: Effect of addition of various sulfated polysaccharides to reaction solution on reactivity of soluble interleukin-2 receptor.

The measurement was carried out in accordance with Referential Example 1, except for the following description.

Specimen dilution solution: A buffer containing 0.1 mol/L HEPES (8.0), 0.15 mol/L NaCl, 0.05% Tween20, and 0.4 mmol/L ethylenediaminetetraacetic acid was used.

Dextran sulfate (molecular weight: 20,000) was added to the specimen dilution solution so as to be each concentration (0.0000004, 0.000004, 0.00004, 0.0004, 0.004, 0.04%) in the reaction solution.

Dextran sulfate (molecular weight: 4,000) was added to the specimen dilution solution so as to be each concentration (0.000004, 0.00004, 0.0004, 0.004, 0.04%) in the reaction solution.

β-Cyclodextrin sulfate was added to the specimen dilution solution so as to be each concentration (0.004, 0.01, 0.02, 0.04, 0.08, 0.2, 0.4%) in the reaction solution.

Standard: A dilution series obtained by diluting recombinant sIL-2R so as to be 100000, 40000, 2500, 500, and 0 U/mL was used. In this dilution, a buffer containing 0.05 mol/L PBS (7.4), 0.05% Tween20, 0.1% BSA, and 0.05% sodium azide was used. The standard was used to calculate each concentration (U/mL) from each luminescence count in accordance with a known method.

The results are shown in Table 2. The value obtained by dividing the concentration of the heparinized plasma by the concentration of the serum and then multiplying it by 100 was shown as heparinized plasma/serum. In the case of no addition, it was found that the reactivity of the soluble interleukin-2 receptor was different from each other, between the serum and the heparinized plasma.

As a result, when the range that was considered to be consistent was defined as −10% to +10%, it was confirmed that the reactivity of the soluble interleukin-2 receptor in the serum was consistent with that in the heparinized plasma by adding 0.000004% or more of dextran sulfate (molecular weight: 20,000), 0.0004% or more of dextran sulfate (molecular weight: 4,000), or 0.004% or more of β-cyclodextrin sulfate.

TABLE 2

| Dextran sulfate (molecular weight: 20,000) | | | | | | | |
|---|---|---|---|---|---|---|---|
| | Concentration of sulfated polysaccharide (%) | | | | | | |
| | 0 | 0.0000004% | 0.000004% | 0.00004% | 0.0004% | 0.004% | 0.04% |
| Serum sample (U/mL) | 119 | 185 | 224 | 259 | 259 | 270 | 271 |
| Heparinized plasma serum (U/mL) | 142 | 223 | 223 | 247 | 252 | 266 | 267 |
| heparinized plasma/serum | 119% | 121% | 100% | 95% | 97% | 99% | 99% |

| Dextran sulfate (molecular weight: 4,000) | | | | | | |
|---|---|---|---|---|---|---|
| | Concentration of sulfated polysaccharide (%) | | | | | |
| | 0 | 0.000004% | 0.00004% | 0.0004% | 0.004% | 0.04% |
| Serum sample (U/mL) | 119 | 175 | 176 | 217 | 259 | 262 |
| Heparinized plasma serum (U/mL) | 142 | 217 | 217 | 235 | 245 | 249 |
| heparinized plasma/serum | 119% | 124% | 123% | 108% | 95% | 95% |

| β-Cyclodextrin sulfate | | | | | | | | |
|---|---|---|---|---|---|---|---|---|
| | Concentration of sulfated polysaccharide (%) | | | | | | | |
| | 0.000% | 0.004% | 0.01% | 0.02% | 0.04% | 0.08% | 0.2% | 0.4% |
| Serum sample (U/mL) | 119 | 147 | 161 | 173 | 170 | 180 | 192 | 191 |
| Heparinized plasma serum (U/mL) | 142 | 149 | 174 | 175 | 168 | 162 | 174 | 189 |
| heparinized plasma/serum | 119% | 101% | 108% | 101% | 99% | 90% | 91% | 99% |

Comparative Example 1: Effect of addition of polysaccharides without a sulfate group and compounds without a polysaccharide but having a sulfate group to reaction solution on reactivity of sIL-2R.

A polysaccharide without a sulfate group and a compound without a polysaccharide but having a sulfate group were simultaneously added to the reaction solution in order to examine whether or not they exhibited reactivity similar to sulfated polysaccharides. The measurement was carried out in accordance with Referential Example 1, except that a polysaccharide without a sulfate group and a compound without a polysaccharide but having a sulfate group were added to the specimen dilution solution so as to be the following concentrations.

Compounds without a polysaccharide but having a sulfate group: NDSB-195, NDSB-201, and NDSB-256 were individually added to the specimen dilution solution so as to be 0.385 mmol/L and 3.85 mmol/L.

Mixing of a compound without a polysaccharide but having a sulfate group and a polysaccharide without a sulfate group: NDSB-195 and dextran (molecular weight: 2000) were added to the specimen dilution solution so as to be 3.85 mmol/L and 0.19%, respectively.

The results are shown in Table 3. The value obtained by dividing the concentration of the heparinized plasma by the concentration of the serum and then multiplying it by 100 was shown as heparinized plasma/serum. As a result, it was found that the measured value of the serum was inconsistent with that of the heparinized plasma in the case of the compounds without a polysaccharide but having a sulfate group, and that the measured values were inconsistent with each other when the polysaccharide without a sulfate group was further added thereto.

In the case of the coexistence of the polysaccharide without a sulfate group and the compound without a polysaccharide but having a sulfate group, the effects similar to those of the polysaccharides having sulfate groups in Examples 1 and 2 were not obtained. It was an unexpected result, because such high effects could be obtained in the presence of the polysaccharide having sulfate groups, and could not be obtained in the coexistence of the sulfate group and the polysaccharide.

TABLE 3

| | Compound | | | | | | | |
|---|---|---|---|---|---|---|---|---|
| | No addition | NDSB-195 | | NDSB-201 | | NDSB-256 | | NDSB-195 + dextran (2000) |
| | Concentration | | | | | | | |
| | — | 3.85 mM | 0.385 mM | 3.85 mM | 0.385 mM | 3.85 mM | 0.385 mM | 3.85 mM + 0.19% |
| Serum sample (count) | 5352 | 5476 | 5388 | 5317 | 5352 | 5390 | 5200 | 5822 |
| Heparinized plasma serum (count) | 6619 | 6943 | 7173 | 6678 | 7143 | 7115 | 7055 | 7617 |
| heparinized plasma/serum | 124% | 127% | 133% | 126% | 133% | 132% | 136% | 131% |

Example 3: Effect of addition of sulfated polysaccharide to reaction solution on reactivity of total PSA.

Example 3-1: Preparation of reagent for measuring total PSA and samples to be measured.

A reagent for measuring total PSA was prepared.

Specimen dilution solution: A buffer containing 0.1 mol/L HEPES (8.0), 0.15 mol/L NaCl, and 0.05% Tween20 was used.

First antibody solution: A magnetic-particle solution containing magnetic latex particles (JSR) on which a mouse monoclonal antibody (manufactured by Biospacific) that recognized PSA was immobilized was used.

Second antibody solution: A labeled-antibody solution containing another mouse monoclonal antibody (manufactured by Biospacific) that recognized PSA and was labeled with alkaline phosphatase (ALP) by a maleimide method was used.

Luminescent substrate solution: CDP-star (manufactured by Applied Biosystems) was used.

B/F washing solution: A buffer containing 0.01 mol/L MOPS (7.5), 0.15 mol/L NaCl, and 0.05% Triton X-100 was used.

β-Cyclodextrin sulfate was added to the specimen dilution solution so as to be each concentration (0.002, 0.004, 0.008, and 0.031%) in the reaction solution.

Samples to be measured (specimens): A serum and heparinized plasma obtained from a healthy person in accordance with a conventional method were used.

Standard: A dilution series obtained by diluting recombinant PSA so as to be 100, 50, 10, 1, and 0 ng/mL was used. In this dilution, a buffer containing 0.01 mol/L MOPS (7.0), 0.15 mol/L NaCl, 0.05% TritonX, and 0.05% Proclin300 was used. The standard was used to calculate each concentration (ng/mL) from each luminescence count in accordance with a known method.

Example 3-2: Measurement with reagent for measuring total PSA and results.

The measurement was carried out in a similar fashion to Referential Example 1-2, expect that the subject to be measured was total PSA.

The results are shown in Table 4. The value obtained by dividing the concentration of the heparinized plasma by the concentration of the serum and then multiplying it by 100 was shown as heparinized plasma/serum. In the case of no addition, it was found that the reactivity of the total PSA was different from each other, between the serum and the heparinized plasma. Further, when the range that was considered to be consistent was defined as −10% to +10%, it was confirmed that the reactivity of the total PSA in the serum was consistent with that in the heparinized plasma by adding 0.002% or more of β-cyclodextrin sulfate.

TABLE 4

| | β-Cyclodextrin sulfate | | | | |
|---|---|---|---|---|---|
| | Concentration of sulfated polysaccharide (%) | | | | |
| | 0.000% | 0.031% | 0.008% | 0.004% | 0.002% |
| Serum sample (ng/mL) | 0.48 | 0.54 | 0.54 | 0.58 | 0.53 |
| Heparinized plasma serum (ng/mL) | 0.56 | 0.58 | 0.58 | 0.59 | 0.54 |
| heparinized plasma/serum | 116% | 107% | 106% | 101% | 103% |

INDUSTRIAL APPLICABILITY

According to the present invention, when a substance to be measured (for example, sIL-2R) is detected, in particular, regardless of the type of specimen generally used (a serum and heparinized plasma), it is possible to stably obtain the measurement result with high accuracy, unaffected by interfering substances in the specimen. Clinical tests need to be measured conveniently and quickly, and they are also measured not only in the laboratory but also in the POCT field and the like. For example, when targeting blood samples, considering the possibility of being able to be measured under various circumstances, since the containers used to collect the samples are diverse, regardless of the type of obtained specimen, in particular, when a generally used serum or heparinized plasma is used, the present invention in which the measurement result can be stably obtained with high accuracy is particularly useful.

Although the present invention has been described with reference to specific embodiments, various changes and modifications obvious to those skilled in the art are possible without departing from the scope of the appended claims.

The invention claimed is:

1. A method of immunologically measuring a substance to be measured in a biological sample, said method comprising:
    providing a sample selected from the group consisting of a blood sample to which heparin is added as an anticoagulant, and a serum sample;
    bringing the sample into contact with an antibody that specifically binds to the substance to be measured in the presence of 0.002% to 0.4% β-cyclodextrin sulfate to form an immunocomplex; and
    analyzing the immunocomplex or a signal derived from the immunocomplex.

2. The method according to claim 1, wherein β-cyclodextrin sulfate is contained in a solution for diluting specimen and/or an antibody solution.

3. The method according to claim 1, wherein the said analyzing comprises the step of separation of bound and free (B/F) of the formed immunocomplex.

4. The method according to claim 1, wherein the step of bringing the substance into contact with an antibody comprises contacting with a second antibody that specifically binds to the substance to be measured.

5. The method according to claim 1, wherein the substance to be measured is soluble interleukin-2 receptor or prostate specific antigen.

* * * * *